United States Patent [19]

Brookfield

[11] 4,300,563
[45] Nov. 17, 1981

[54] REUSABLE BABY NAPKIN

[76] Inventor: Helen K. Brookfield, 36 Moorhouse St., Camberwell East, Victoria 3124, Australia

[21] Appl. No.: 159,676

[22] Filed: Jun. 16, 1980

Related U.S. Application Data

[63] Continuation-in-part of Ser. No. 900,154, Apr. 16, 1978, abandoned.

[51] Int. Cl.³ .............................................. A41B 13/02
[52] U.S. Cl. .................................................... 128/287
[58] Field of Search ............ 128/284, 286, 287, 290 H

[56] References Cited

U.S. PATENT DOCUMENTS

| | | | |
|---|---|---|---|
| D. 179,397 | 12/1956 | Seydler . | |
| 2,545,216 | 3/1951 | Toussle | 128/287 |
| 2,599,355 | 6/1952 | Stepp | 128/287 |
| 2,691,893 | 10/1954 | Bernard | 128/284 |
| 2,898,912 | 8/1959 | Adams | 128/284 |
| 2,910,982 | 11/1959 | Woodward | 128/284 |
| 3,049,124 | 8/1962 | Thompson | 128/287 |
| 3,322,122 | 5/1967 | Daniel | 128/284 |
| 3,407,813 | 10/1968 | Grippo et al. | 128/287 |
| 3,563,242 | 2/1971 | Hedstrom et al. | 128/287 |
| 4,018,226 | 4/1977 | Korgemets | 128/287 |

FOREIGN PATENT DOCUMENTS 68065  3/1958  France .

*Primary Examiner*—C. Fred Rosenbaum
*Attorney, Agent, or Firm*—Andrus, Sceales, Starke & Sawall

[57] ABSTRACT

The present invention provides a baby's napkin for a baby comprising a relatively moisture impervious outer layer and a relatively moisture absorbent inner layer secured to one another and having extended portions adapted to be tied together to secure the napkin to a baby.

7 Claims, 8 Drawing Figures

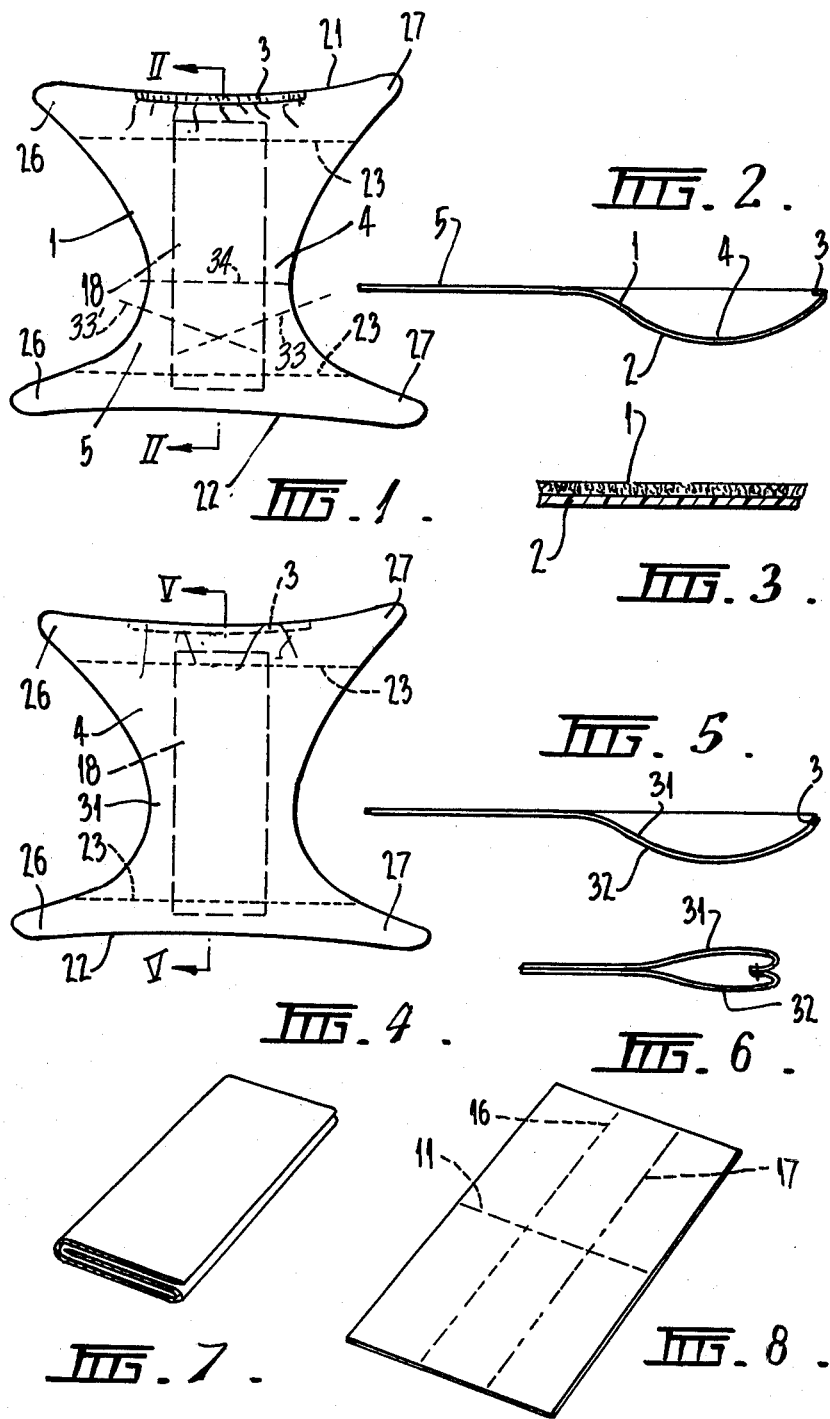

REUSABLE BABY NAPKIN

CROSS REFERENCE TO RELATED APPLICATION

The present application is a continuation-in-part application of U.S. patent application Ser. No. 900,154, filed Apr. 16, 1978 and now abandoned.

BACKGROUND OF THE INVENTION

The present invention relates to an improved reusable baby napkin.

It is known to wrap babies in fabric diapers, but these can become wet through. Pins are required and are dangerous.

It is also known to use disposable nappies comprising an outer shield of sheet plastics material and an inner pad of absorbent material. However, these, to the best of my knowledge, have always had a portion of the outer shield folded over the inner pad such that the outer shield is often in contact with wet areas of a baby.

It is also known to use disposable nappies comprising a re-usable outer shield of sheet plastics material known as a snib and a disposable inner pad of absorbent material. Once again, the outer shield usually folds over the inner pad and, further, the outer shields tear easily and often leak.

There is thus a need for a durable, reusable, effective, inexpensive, outer wrapper which can be used in conjunction with disposable absorbent material or re-usable fabric nappies.

SUMMARY OF THE PRESENT INVENTION

The present invention provides a baby's napkin comprising a relatively moisture impervious outer layer and a relatively moisture absorbent inner layer secured to one another and having extending portions adapted to be tied together about and to secure the napkin to a baby.

The relatively moisture impervious outer layer may be sheet or woven plastics material or any other relatively moisture impervious material. The relatively moisture absorbent inner layer is preferably a fabric of natural origin and may be a woven, knitted or non-woven material. The fabric of natural origin is preferably cotton; preferred is a flannelette or knitted cotton material.

The inner and outer layers are preferably secured to one another at least along the perimeter of one thereof. It is to be noted that it is preferred that the inner and outer layers are of substantially the same size and shape so that neither is substantially folded over the other. In this respect, however, a fold of up to ½ inch is generally tolerable although less is desirable.

In one instance, the inner and outer layers are a bonded material. In another instance, the inner and outer layers are sewn to one another about their perimeters.

The sides of the layers are inwardly concavely curved along their entire length in a modified hyperbolic form to provide a narrow central portion straddled by the baby. The transverse axes of the hyperbolic-like curves of the sides intersect at an angle of less than 180°, preferably between 150°–120°, and still more preferably 140°. The layout of the napkin is thus non-symmetrical about a crosswise line intersecting the sides in the narrow central portion so that the napkin is fuller in back than in front to accommodate the buttocks of the baby.

This fullness may conveniently be enhanced by introducing elastic into the central portion of the waist region.

In use, a further absorbent material will be enclosed within the napkin on the textured surface of the inner layer. This may be a disposable pad such as a pad of wood derived cellulose material such as that known under the Registered Trade Mark Dri-Tot or may be a conventional cotton or flannelette nappy. It is preferred to use a full size or half of a standard size nappy folded into 6 or 12 layers in an 8"×10" pad.

A particular advantage of this invention is that contact of wet areas of a baby with synthetic plastics material is reduced as compared to many previous attempts. However, the advantages of a snib are retained and even improved upon by reason of an increased durability which is easily had.

BRIEF DESCRIPTION OF THE DRAWING

Specific babies' napkins in accordance with the present invention will now be described with the aid of the accompanying drawings in which:

FIG. 1 is a plan view of the inside of one embodiment of the napkin according to the present invention;

FIG. 2 is a cross-section taken along the line II—II of FIG. 1;

FIG. 3 is a detail cross-section of the napkin of FIG. 1;

FIG. 4 is a plan view of the inside of another embodiment of the napkin, according to the present invention;

FIG. 5 is a cross-section taken along the line V—V of FIG. 4;

FIG. 6 is a cross-sectional detail of the napkin of FIG. 4;

FIG. 7 shows a pad suitable for use with either of the napkins; and

FIG. 8 shows the manner in which the pad is obtained by folding.

DETAILED DESCRIPTION

The baby's napkin shown in FIGS. 1–3 is made in the shape shown of a moisture absorbent, knitted cotton material 1 bonded to a moisture impervious sheet plastics material 2. The bonding is substantially over the whole area of contact of the two materials.

The sides of the napkin curve concavely inward along their entire length in a modified hyperbolic-like form. The ends of the napkin curve arcuately inward to a lesser extent. The sides and ends define extended portions 26 and 27.

The transverse axes 33 and 33' of the modified hyperbolic-like curves of the sides intersect at an angle of less than 180°, preferably between 150°–120° and still more preferably 140°. The napkin is thus non-symmetrical about a crosswise line 34 intersecting the sides in the narrow central portion so that the napkin is fuller in back than in front. This reduced size in front avoids gapping or leaking in front while the fullness in back accommodates the buttocks of the baby.

Elastic 3 is sewn to the napkin in the central portion of the rear end and in consequence enhances the fullness of the napkin at the buttocks area 4 and makes the napkin relatively constricted in the waist back area to avoid leaks.

In use, a conventional nappy is cut in half and seamed and will appear as in FIG. 8. That halved napkin is then folded along the line 11 and thereafter is folded along the lines 16 and 17 to form the pad shown in FIG. 7. A whole nappy may be used in lieu.

The pad is then placed on the napkin as shown by dash outline 18 in FIG. 1. The shape and construction of the napkin, as well as the exposed, textured surface of knitted layer 1 are highly effective in retaining the pad on the layer. If desired, the napkin ends 21 and 22 may be folded over the pad as indicated by dash lines 23. Alternatively, pockets may be provided to receive the ends of the pad.

The assembly so formed is positioned on a baby and the corner portions 26 and 27 formed by the curved sides and ends are tied to one another to secure the assembly on the baby.

The napkin shown in FIGS. 4–6 is similar to that shown in FIGS. 1–3 and like numerals denote like parts. It differs, however, in being formed of an outer sheet of woven nylon material 32 and an inner sheet of moisture absorbent flannelette 31 which are sewn together about their perimeters as shown in FIG. 6 and in that the elastic is provided between the materials 31 and 32.

The napkin shown in FIGS. 4–6 is used similarly to that shown in FIGS. 1–3.

The above described napkins have the advantage that a soft natural material is adjacent the baby and yet the waterproof advantages of plastics materials is obtained, safety pins or studs are not required as tying is used and this allows for easy adjustment to the size of a particular baby, the napkin can be re-used several times with different pads before needing to be washed (on average about three napkins are used per day), although a similar number of pads to conventional nappies might be used each day, each pad, when unfolded, is smaller than a conventional nappy.

Further, the napkins are easy to make and are durable.

Modifications and adaptations may be made to the above described without departing from the spirit and scope of this invention which includes every novel feature and combination of features disclosed herein.

The claims form part of the disclosure of this Specification.

Various modes of carrying out the invention are contemplated as being within the scope of the following claims particularly pointing out and distinctly claiming the subject matter which is regarded as the invention.

I claim:

1. A baby's reusable napkin for receiving a replaceable diaper, comprising: a moisture impervious outer layer and a relatively moisture absorbent inner layer having an exposed textured surface for receiving and retaining the replaceable diaper, said layers being substantially the same size and shape and secured to one another, said layers have opposing sides inwardly concavely curved along their entire length in a modified hyperbolic-like form to provide a narrow central portion straddled by the baby when the napkin is worn, the transverse axes of the hyperbolic-like curves of said sides converging toward the front of said napkin and intersecting at an angle of less than 180°, said curved sides to configuring said napkin that it is non-symmetrical about a crosswise line intersecting said sides in said narrow central portion to provide a greater area to the region of the napkin that, in use, will be adjacent the buttocks and back of the baby than to the region that will be in front, said layers having both ends arcuately inwardly curved to a lesser extent than said sides, said end of said napkin that, in use, will be adjacent the waist at the back of the baby containing an elastic construction centrally located on said end for providing a fullness to the napkin in the region that, in use, will be adjacent the buttocks of the baby, said curved ends and sides forming corner portions sufficiently extended as to permit them to be tied together about the baby for securing the napkin to the baby.

2. A napkin as claimed in claim 1 wherein the transverse axes of the hyperbolic-like curves of said sides intersect at an angle of between 150° and 120°.

3. A napkin as claimed in claim 2 wherein the transverse axes of the hyperbolic-like curves of said sides intersect at an angle of 140°.

4. A napkin as claimed in claim 1 wherein the relatively moisture impervious outer layer is made of sheet or woven synthetic plastics material.

5. A napkin as claimed in claims 1 or 4 wheren the relatively moisture absorbent inner layer is made of a woven, knitted, or non-woven fibrous material.

6. A napkin as claimed in claim 1 wherein the inner and outer layers are bonded to one another over their entire abutting surfaces.

7. A napkin as claimed in claim 1 wherein the inner and outer layers are secured together along their peripheries.

* * * * *